Figure 1:
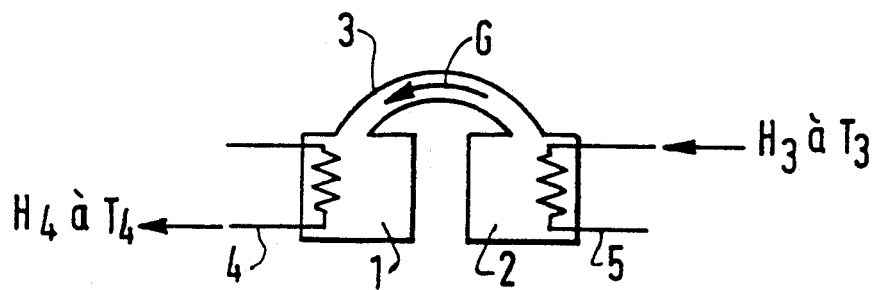

United States Patent [19]

Oms et al.

[11] Patent Number: 4,994,394

[45] Date of Patent: Feb. 19, 1991

[54] METHOD OF USING A THERMAL SHOCK PROBE, A THERMAL SHOCK PROBE USABLE IN THE METHOD AND APPLICATION OF THIS METHOD

[75] Inventors: Jean-Luc Oms, Villelongue Dels Monts; Jacques Prosdocimi, Canottes; Maurice Comtat, Toulouse, all of France

[73] Assignee: Societe Nationale Elf Aquitaine, Courbevoie, France

[21] Appl. No.: 239,664

[22] Filed: Sep. 2, 1988

[30] Foreign Application Priority Data

Sep. 7, 1987 [FR] France ............................. 87 12390

[51] Int. Cl.$^5$ ............................................. G01N 35/08
[52] U.S. Cl. ....................................... 436/55; 436/147; 436/150; 436/151; 422/95
[58] Field of Search ................... 422/78, 95; 436/147, 436/150, 151, 55

[56] References Cited

U.S. PATENT DOCUMENTS

| 4,147,515 | 4/1979 | Haas et al. ........................... 436/151 |
| 4,592,896 | 6/1986 | Runnells et al. ................... 422/95 X |
| 4,783,317 | 11/1988 | Kuerzinger et al. ........... 436/147 X |

FOREIGN PATENT DOCUMENTS

| 2808464 | 9/1978 | Fed. Rep. of Germany . |
| 3122642 | 12/1982 | Fed. Rep. of Germany . |
| 2546278 | 11/1984 | France . |

*Primary Examiner*—Charles Hart
*Attorney, Agent, or Firm*—Oblon, Spivak, McClelland, Maier & Neustadt

[57] ABSTRACT

The present invention provides a method of using a thermal shock probe, such a thermal shock probe and application of this method to the control of a heat pump. The method of using a thermal shock probe formed of a thermocouple associated with a heating element, is characterized in that it is used for monitoring, in a solid-gas reactor (1,2), the chemical reaction between a porous mixture and a gas by applying a heat flux variation and processing the response of the thermocouple.

11 Claims, 3 Drawing Sheets

METHOD OF USING A THERMAL SHOCK PROBE, A THERMAL SHOCK PROBE USABLE IN THE METHOD AND APPLICATION OF THIS METHOD

The present invention relates to a method of using a thermal shock probe, a thermal shock probe usable in the method and application of this method to the control and monitoring of chemical heat pumps.

From the patent application FR 85 19137 the use of a thermal shock probe is known formed of a thermocouple associated with a heating element for measuring the thermal conductivity and the local heat capacity of materials subjected to any thermal and hydrous conditions. This use is anticipated in particular for studying constructional materials, consolidated or not and formed of porous granular solids which may undergo variable humidities.

A first object of the invention is to provide a method of using a thermal shock probe in applications other than the simple measurement of the thermal characteristics of the materials.

This object is reached by the fact that the method of using a thermal shock probe, formed of a thermocouple associated with a heating element, is characterized in that the probe is used for monitoring, in a solid-gas reactor, the chemical reaction between a porous mixture and a gas by applying a heat flow variation and processing the response of the thermocouple.

A second object of the invention is to provide a use making it possible to have a minimum response time in applications to a solid-gas reactor.

This second object is reached by the fact that the method of use is characterized in that the application of the heat flow variation is formed by a thermal pulse obtained by a current generator feeding the heating resistance, when the solid of the reactor is a mixture of salt and an inert binder, for example expanded graphite and processing is provided by integrating the response curve of the thermocouple.

Another object is to provide a method of use of reactors other than those using such a mixture.

This object is reached by the fact that the method of use is characterized in that the heat flow variation is formed by a thermal level obtained by feeding the heating resistance by means of a current generator, generating a current level and processing is provided by detecting a temperature level at a given time.

Another object of the invention is to provide a method of use applicable whatever the structure of the reactor and making it possible to measure a heterogeneity in the reactor.

This object is reached by the fact that the method of use is characterized in that several probes are disposed radially in a reactor having, for example, a sandwich, plate modular structure or are disposed in directions parallel to an axis of symmetry of the structure of the reactor, for reactors having another structure.

Another object of the invention is to provide a thermal shock probe particularly well adapted to the method of use in a reactor.

This object is reached by the fact that the thermal shock probe, comprising a hollow cylindrical tube, closed at one end, a heating resistance extending through the whole tube, is characterized in that the tube is made from stainless steel, the heating resistance is isolated from the tube by magnesium oxide and in that at least one thermocouple is disposed close to the tube.

According to another characteristic, the thermocouple is welded to the tube.

Another object of the invention is to provide an application of the method of using a thermal shock probe for controlling and monitoring chemical heat pumps.

This object is reached by the fact that the chemical pump is formed of one or more solid-gas reactors each incorporating at least one thermal probe and by the fact that the signals delivered by the thermocouple are used for controlling and monitoring the operation of the heat pump.

According to another characteristic, the signals from the thermocouple are used for stopping a storage step or a destorage step.

According to a last characteristic, the signals from the thermocouple are used for controlling the reversal of operation of the reactors.

Figure 2:
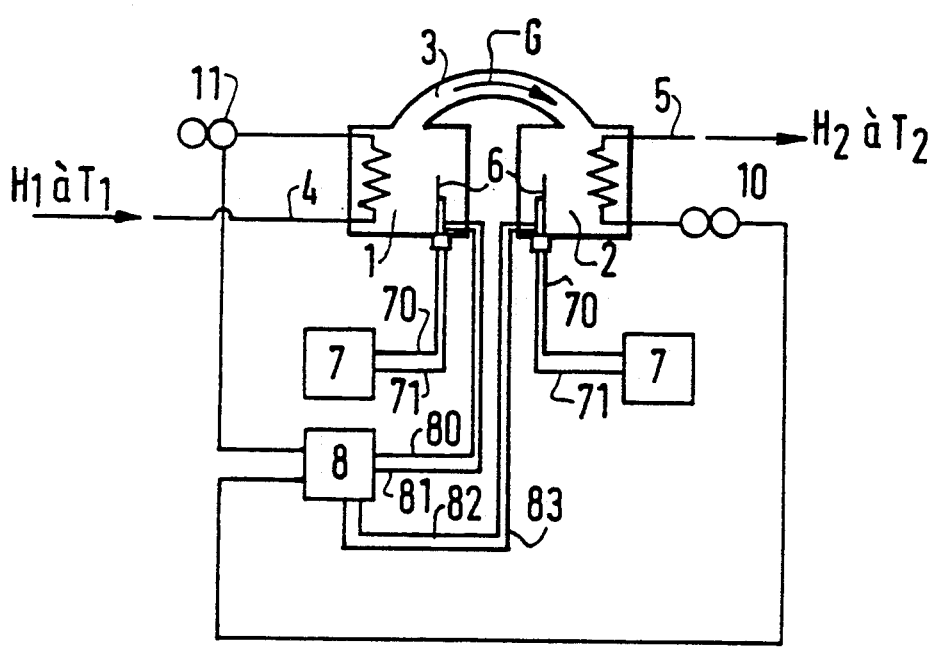
Figure 4:
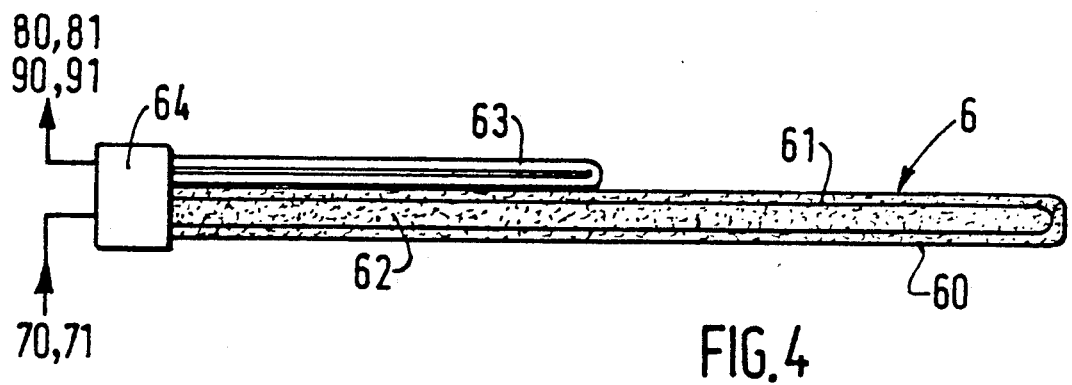
Figure 3:
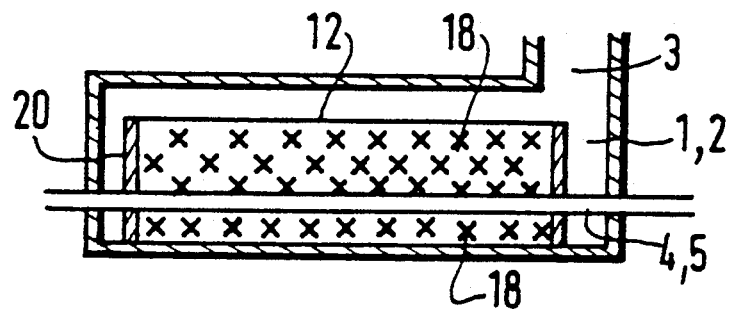
Figure 5:
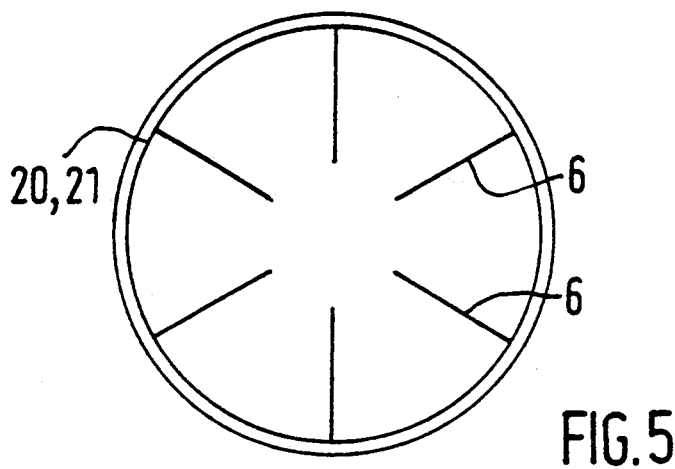
Figure 6:
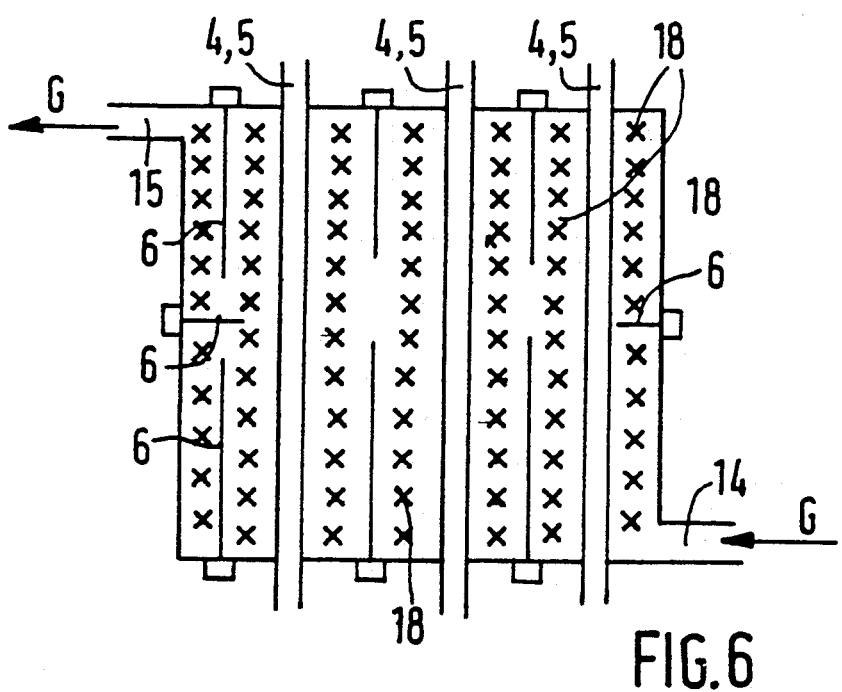
Figure 7:
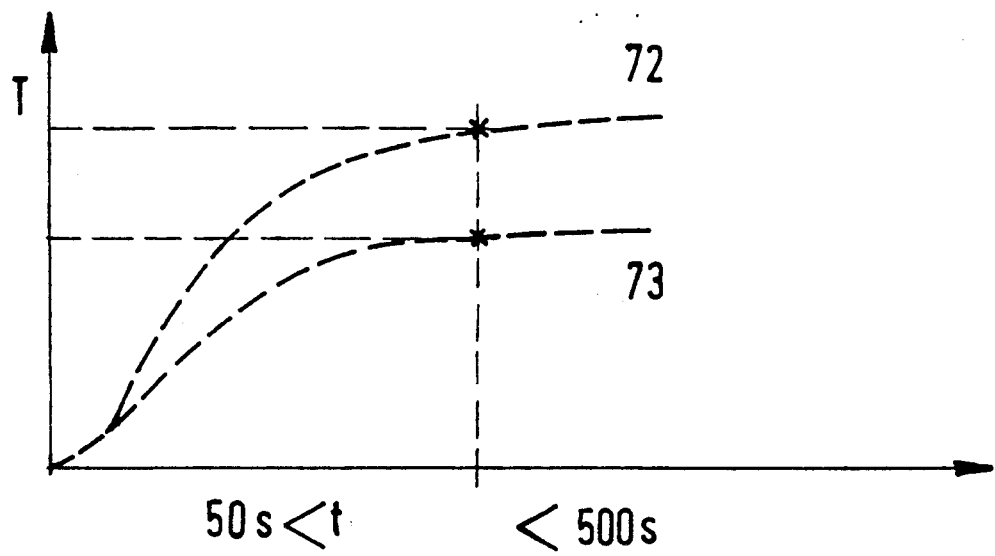

Other characteristics and advantages of the present invention will be clear from the following description, with reference to the accompanying drawings in which:

FIG. 1 shows schematically a heat pump formed of solid-gas reactors during the heat production phase, FIG. 2 shows schematically the same pump during the regeneration phase, FIG. 3 shows in section a modular plate reactor structure, FIG. 4 shows a sectional view of a thermal shock probe of the invention, FIG. 5 shows a top view in section of a plate reactor, FIG. 6 shows a sectional view of another solid-gas reactor structure, FIG. 7 shows a response diagram of a probe during operation of a reactor, and FIG. 8 shows response diagrams of the probe during operation of a solid-gas reactor.

In FIG. 1 a heat pump has been shown schematically during the phase for destoring the energy, and in FIG. 2 the same pump during the storage phase. The heat pump comprises two solid-gas reactors 1, 2 connected together by a pipe 3 through which the gas flows. The solid may for example be a salt-expanded graphite mixture with calcium chloride $CaCl_2$ as salt and the gas, for example, methylamine. Each reactor has at least one heat exchanger 4, 5 for exchanging heat between the reaction medium and the external heat sources.

The device operates in the following way.

In a regeneration step, heat H1 at temperature T1 is supplied to the reactor 1. A chemical reaction in the solid-gas reactor 1 produces gas G at the pressure P1. This gas is fed into reactor 2 by pipe 3 at the same pressure. There then occurs in reactor 2 a reaction at a temperature T2 which supplies the heat H2. During a heat supply step, heat H3 is delivered at a temperature T3. The reaction takes place in the direction of gas production at the pressure P3 in reactor 2. When the gas passes through reactor 1, the latter reacts in the exothermic direction so as to supply heat H4 at temperature T4.

The problem which arises in such high efficiency chemical heat pumps is to know the advance of the gas-solid reaction so as to be able to monitor and control such a chemical heat pump. The solution used must allow a considerable range of variation for determining the advance of the reaction with good accuracy. Furthermore, the measurement must be able to be carried out in situ in a short time with respect to the reaction time of the reactor without for all that disturbing the operation of the system.

The solution has been provided by using the thermal shock probe shown in FIG. 4. This probe 6 is formed of a tube 60 made from stainless steel for withstanding the corrosion of the salt-graphite mixture and the gas. Tube 60 is cylindrical and closed at one end. In this tube, a heating filament 61 is disposed which is connected by its two ends to the wires 70, 71 bringing current from a supply source, shown in FIG. 2 by the reference 7. The whole of the heating element 61 is isolated from tube 60 by magnesium oxide 62 placed inside the tube.

In a preferred embodiment of the invention, a thermocouple 63 is welded to the external face of the heating tube 60. This thermocouple is connected by wires 80, 81 to a signal recording and processing circuit.

In a variant, not shown, of the thermal probe, the thermocouple may be placed at a given distance from the heating tube and connected to this tube solely by the insulating plug 64. In this variant, several thermocouples may be disposed in a volume about the heating tube.

Such a thermal shock probe may be used in modular plate structure reactors, such a shown schematically in FIGS. 3 and 5. In a reactor of this type, the gas arrives through the orifice 3 into an enclosure 12. In this enclosure 12 is placed an exchanger 4, 5 on which rests a cylindrical skirt 20 in which a salt-graphex mixture 18 is disposed as solid. Under the exchanger 4, 5 will also be disposed, in modular skirts 21, the same porous salt-expanded graphite mixture. Such a reactor may, in a way known per se, have a succession of heat exchanger stages and solid layers. For further details concerning these reactors, reference may be made to the French patent application filed concurrently herewith by the S.N.E.A. and entitled "Fixed bed solid-gas reactor and use of such a reactor in thermochemical heat pumps".

A plurality of thermal shock probes 6 are disposed radially (FIG. 5) inside the skirt 20 or the skirt 21 surrounding the exchangers.

Similarly, in use with reactors such as the one shown in FIG. 6, formed of a cylindrical enclosure in which several tubes 4, 5 are placed for the flow of the heat-carrying fluid, parallel to the axis of symmetry of the enclosure, this enclosure being filled with a salt-expanded graphite mixture 18 and fed through orifice 14 with a gas at a given pressure which is discharged through orifice 15. In an enclosure of this type, the probes 6 may be disposed parallel to the axis of symmetry of the enclosure and to the axis of symmetry of the exchanger elements. Other probes situated in the median part of the enclosure may also be disposed radially, as shown in FIG. 6. The use of several probes distributed as shown for example in FIGS. 5 or 6 in the structure of the reactor makes it possible to measure heterogeneity of the mixture in the reactor.

The device required for implementing the method of using the thermal shock probe and its application to the control of a heat pump is shown in FIG. 2. In each of the reactors 1, 2, at least one thermal shock probe will be placed such as the one which has just been described, this probe being fed by an electric current generator 7 for creating the heat flow required for the measurement. This electric current generator will generate either a current level or a current pulse. The response signals of the thermocouple placed in reactor 1 are transmitted by wires 80, 81 to a signal processing circuit 8. Similarly, the response of the thermocouple 6 placed in the second reactor 2 will be conveyed by wires 82, 83 to this circuit 8 for processing the signals of the thermocouples. This circuit 8 will make it possible for example to control the electrovalves 11, 10 either for stopping a heat production or regeneration phase or reversing the operating cycle of the reactors by causing them to pass from one phase to the other.

Such a use of a thermal probe for such a control has been made possible by the discovery that the response of a thermocouple to thermal excitation was representative of the advance of the reaction in the reactor. Calibration of the sensor carried out in situ makes possible a direct correlation between the analyzed signal and the composition of the reaction mixture. Thus, FIG. 7 shows the response curves of the thermocouple as a function of the evolution of the reaction when a thermal excitation has been fed to the sensor corresponding to a current level. Curve 72 shows, for example, an initial state of the reactor whereas curve 73 shows a composition corresponding to a different reaction mixture. Thus, detection of the temperature level at a given time within a range of 50 to 500 seconds will be sufficient for analyzing the evolution of the reaction and controlling it by controlling the heat pump.

Figure 8A:
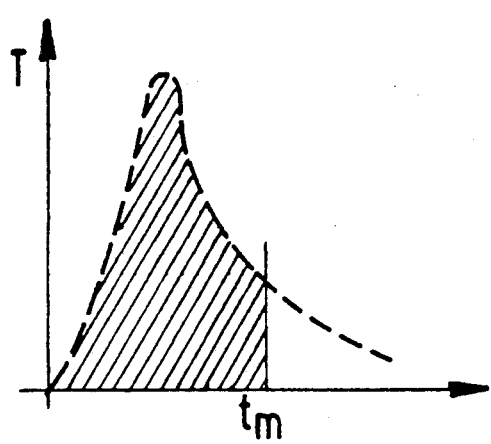
Figure 8B:
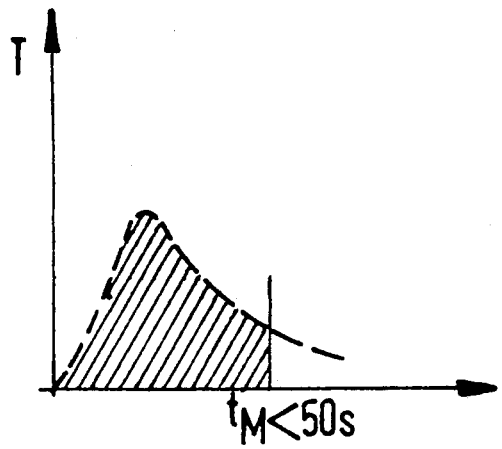

Similarly, when it is desired to work with a shorter measurement time, for controlling the system, the analysis of the response of the medium to a thermal pulse will be effected by integrating the response curve of the thermocouple. This method makes it possible to have measurement times less than 50 seconds. The difference of area between FIGS. 8A and 8B represents the evolution of the reaction. Thus, FIG. 9A corresponds to a discharged salt whereas FIG. 8B corresponds to a charged salt.

Finally, such a method of using a thermal shock probe is particularly well adapted to solid-gas reactors use in heat pumps for the latter cause swelling of the salt during the first absorption of gas. Such swelling of the salt makes it possible to eliminate, even disregard, the thermal probe-solid contact resistance. This thermal resistance is very often one of the main obstacles in the use of this type of probe in other applications.

Furthermore, such a method of using a thermal shock probe has advantages with respect to other conventional methods such as the use of a mass flowmeter or condensed gas measurement. In fact, in the case of a mass flowmeter, the use is delicate, particularly n the case of a condensable gas causing parasite condensation and clogging.

Other modifications within the scope of a man skilled in the art also form part of the spirit of the invention.

We claim:

1. Method of using a thermal shock probe, formed of a thermocouple associated with a heating element, characterized in that the probe is used for monitoring, in a solid-gas reactor (1,2), the chemical reaction between a porous mixture and a gas by applying a heat flux variation and processing the response of the thermocouple.

2. Method of use according to claim 1, characterized in that the application of the heat is formed by a thermal pulse obtained by a current generator (7) feeding the heating resistance (61) so as to obtain short response times and the processing is provided by integrating the response curve of the thermocouple.

3. Method of use according to claim 1, characterized in that application of the heat variation is formed by a thermal level obtained by a current generator (7) feeding the heating resistance (61) with a current level and the processing is provided by detecting a temperature level at a given time.

4. Method of use according to one of the preceding claims, characterized in that several probes are disposed radially.

5. Method of use according to claim 4, characterized in that the probes are disposed in a reactor having a modular sandwich, plate structure.

6. Method of use according to one of claims 1 to 3, characterized in that the probes are disposed along an axis of symmetry of the structure of the reactor.

7. Thermal shock probe comprising a hollow cylindrical tube (60), closed at one end, a heating resistance (61) extending through the whole tube, characterized in that the tube is made from stainless steel, the heating resistance (61) is isolated from the tube (60) by magnesium oxide (62) and in that at least one thermocouple (63) is disposed in the vicinity of the tube.

8. Thermal shock probe according to claim 7, characterized in that the thermocouple is welded to the tube.

9. Application of the method of using a thermal shock probe for controlling and monitoring chemical heat pumps, characterized in that the chemical pump is formed of one or more solid-gas reactors (1,2) each incorporating at least one thermal shock probe (6) and in that the signals delivered by the thermocouple (63) of each probe are used for controlling and monitoring the operation of the heat pump.

10. Application according to claim 9, characterized in that the signals are used for stopping a storage step or a destorage step.

11. Application according to claim 9, characterized in that the signals are used for controlling the reversal of operation of the reactors.

* * * * *